United States Patent

Weichert et al.

[11] Patent Number: 5,547,953
[45] Date of Patent: Aug. 20, 1996

[54] SUBSTITUTED 1-OXO-1,2-DIHYDROISOQUINOLINOYLGUANIDINES AND 1,1-DIOXO-2H-1,2-BENZOTHIAZINOYLGUANIDINES, A PROCESS FOR THEIR PREPARATION, THEIR USE AS MEDICAMENTS OR DIAGNOSTIC AGENTS, AND MEDICAMENTS CONTAINING THEM

[75] Inventors: Andreas Weichert, Egelsbach; Heinz-Werner Kleemann, Bad Homburg; Hans-Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 362,003

[22] Filed: Dec. 22, 1994

[30] Foreign Application Priority Data

Dec. 24, 1993 [DE] Germany .......................... 43 44 550.0

[51] Int. Cl.⁶ .................. C07D 217/22; C07D 279/02; A61K 31/47; A61K 31/54
[52] U.S. Cl. .................. 514/226.5; 514/309; 546/141; 544/49
[58] Field of Search ................ 544/49; 546/141; 514/226.5, 307

[56] References Cited

U.S. PATENT DOCUMENTS

| | | | |
|---|---|---|---|
| 3,780,027 | 12/1973 | Cragoe et al. | 260/349.6 |
| 5,091,394 | 2/1992 | Englert et al. | 514/331 |
| 5,373,024 | 12/1994 | Lang et al. | 514/618 |
| 5,416,094 | 5/1995 | Lal et al. | 514/307 |

FOREIGN PATENT DOCUMENTS

| | | |
|---|---|---|
| 0589336 | 3/1994 | European Pat. Off. . |
| 0602523 | 6/1994 | European Pat. Off. . |

*Primary Examiner*—Mukund J. Shah
*Assistant Examiner*—Matthew V. Grumbling
*Attorney, Agent, or Firm*—Finnegan, Henderson, Farabow, Garrett & Dunner, L.L.P.

[57] ABSTRACT

Substituted 1-oxo-1,2-dihydroisoquinolinoylguanidines and 1,1-dioxo-2H-1,2-benzothiazinoylguanidines, a process for their preparation, their use as medicament or diagnostic agent, and also a medicament containing them. Acylguanidines I

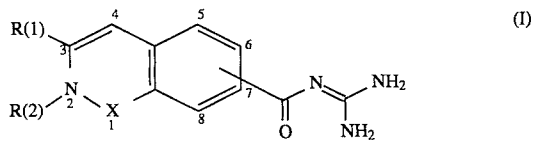

with X equal to carbonyl or sulfonyl; R(1) equal to H, (cyclo)alkyl, phenyl; R(2) equal to H, alkyl, and their pharmaceutically suitable salts, are described. They are obtained by reacting a compound II

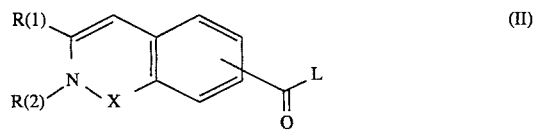

with guanidine. The compounds have no unwanted salidiuretic but very good antiarrhythmic properties. They are able, as a consequence of inhibition of the cellular $Na^+/H^+$ exchange mechanism, to be used for the treatment of all acute or chronic ischemia-induced damage.

18 Claims, No Drawings

SUBSTITUTED 1-OXO-1,2-DIHYDROISOQUINOLINOYLGUANIDINES AND 1,1-DIOXO-2H-1,2-BENZOTHIAZINOYLGUANIDINES, A PROCESS FOR THEIR PREPARATION, THEIR USE AS MEDICAMENTS OR DIAGNOSTIC AGENTS, AND MEDICAMENTS CONTAINING THEM

The invention relates to acylguanidines of the formula I

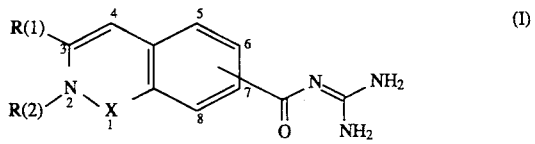

in which:

X is carbonyl, sulfonyl

R(1) is H, $(C_1-C_8)$-alkyl unsubstituted or substituted by hydroxyl, $(C_3-C_8)$-cycloalkyl, phenyl, which is unsubstituted or substituted by 1–3 substituents from the group consisting of F, Cl, $CF_3$, $CH_3$, methoxy, hydroxyl, amino, methylamino or dimethylamino, R(2) is H, $(C_1-C_4)$-alkyl, and the pharmaceutically suitable salts thereof.

Compounds of the formula I in which:

X is sulfonyl,

R(1) is H, $(C_1-C_8)$-alkyl which is unsubstituted or substituted by hydroxyl, $(C_3-C_8)$-cycloalkyl, phenyl, which is unsubstituted or substituted by 1–3 substituents from the group consisting of F, Cl, $CF_3$, $CH_3$, methoxy, hydroxyl, amino, methylamino, dimethylamino, R(2) is H, $(C_1-C_4)$-alkyl and the pharmaceutically suitable salts thereof, are preferred.

Particularly preferred compounds of the formula I are those in which the carbonyl guanidide [—CO—N═C(NH₂)₂] is substituted in position 7 on the particular benzene nucleus.

If one of the substituents R(1) and R(2) contains one or more centers of asymmetry, these can have either the S or the R configuration. The compounds may be in the form of optical isomers, of diastereomers, of racemates or of mixtures thereof.

The specified alkyl radicals can be either straight-chain or branched.

The invention furthermore relates to a process for the preparation of the compounds I, which comprises reacting compounds of the formula II

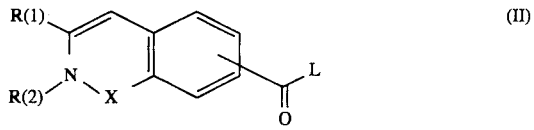

with guanidine, in which X, R(1) and R(2) have the stated meaning, and L is a leaving group which can easily undergo nucleophilic substitution.

The activated acid derivatives of the formula II in which L is an alkoxy, preferably a methoxy, group, a phenoxy group, phenylthio, methylthio, 2-pyridylthio group, a nitrogen heterocycle, particularly 1-imidazolyl, are advantageously obtained in a manner known per se from the underlying carbonyl chlorides (formula II, L=Cl) which for their part can be prepared in a manner known per se from the underlying carboxylic acids (formula II, L=OH) for example with thionyl chloride.

Besides the carbonyl chlorides of the formula II (L=Cl), it is also possible to prepare other activated acid derivatives of the formula II in a manner known per se directly from the underlying carboxylic acid derivatives (formula II, L=OH), such as, for example, the methyl esters of the formula II with L=OCH₃ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl-COOC₂H₅ or tosyl chloride in the presence of triethylamine in an inert solvent, as well as the activation of carboxylic acids with dicyclohexylcarbodiimide (DCC) or with O-[(cyano-(ethoxycarbonyl)methylene)amino]-1,1,3,3-tetramethyluroniumtetrafluoroborate ("TOTU"), [Proceedings of the 21st European Peptide Symposium, Peptides 1990, Editors E. Giralt and D. Andreu, Escom, Leiden, 1991]. A number of suitable methods for preparing activated carboxylic acid derivatives of the formula II are indicated, specifying the source literature, in J. March, Advanced Organic Chemistry, Third Edition (John Wiley & Sons, 1985), p. 350.

The reaction of an activated carboxylic acid derivative of the formula II with guanidine takes place in a manner known per se in a protic or aprotic polar but inert organic solvent. Those which have proven suitable for the reaction of the methyl carboxylates (II, L=OMe) with guanidine are methanol, isopropanol or THF at from 20° C. to the boiling point of these solvents. Most of the reactions of compounds II with salt-free guanidine have advantageously been carried out in aprotic inert solvents such as THF, dimethoxyethane, dioxane. However, water can also be used, employing a base such as, for example, NaOH as solvent in the reaction of II with guanidine. When L=Cl, it is advantageous to add an acid scavenger, for example in the form of excess guanidine, to trap the hydrohalic acid.

The underlying carboxylic acid derivatives of the formula II are unknown and are prepared as follows: derivatives of the formula II (X=SO₂): chlorosulfonation of the particular positional isomers of the bromo or iodo carboxylic acids in pure chlorosulfonic acid at 80°–120° C. for 3–8 h yields the corresponding bromine- or iodine-substituted sulfo chlorides. In order to prepare N-alkyl-substituted sulfonamides [formula IV, R(2) not equal to H], the particular sulfo chloride is reacted with an excess of primary amine or of primary amine hydrochloride in 10N NaOH (aq) at room temperature for 3–6 h. Acidic aqueous workup provides the substituted sulfonamides. In the case of unsubstituted sulfonamides (formula IV, R(2) equal to H), liquid ammonia is used. Finally, compounds of the formula IV are obtained by converting the carboxyl functionality in a known manner into a group —CO—L where L is preferably a methoxy group. The compounds of the formula III are prepared in a manner known per se by introducing the acetylene functionality. For this, liquid substituted acetylenes [R(1) equal to H] are coupled in THF at room temperature in the presence of n-butylamine, copper(I) iodide and catalytic amounts of bis(triphenylphosphine)palladium(II) chloride with compounds of the formula IV. In the case of acetylene [R(1) equal to H], this is passed through the reaction mixture for 3–5 h. The compounds of the formula II are then obtained by the cyclization according to the invention, which is to be carried out at room temperature and is promoted by mercury(II) acetate (0.3eq), in glacial acetic acid in the presence of sulfuric acid as catalyst. Derivatives of the formula II(X=CO): starting from bromo- or iodophthalic acids, the bisamides [formula IV, L=NHR(2)] are prepared in a known manner by in situ generation of the corresponding acid chlorides and subsequent reaction with the particular primary amine [R(2) not equal to H] or liquid ammonia [R(2) equal to H]. The subsequent course of the process corresponds to the preparation, described above, of the benzothiazine derivatives (formula II, X=SO₂).

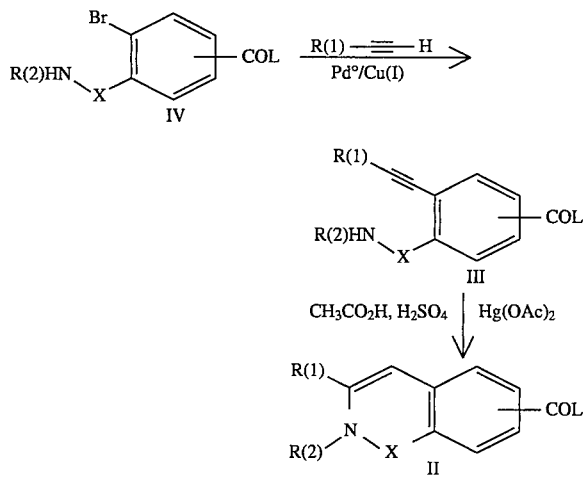

The resulting carboxylic acid derivatives are converted into compounds I according to the invention by one of the process variants described above.

Acylguanidines I are generally weak bases and are able to bind acid to form salts. Suitable acid addition salts are salts of all pharmacologically suitable acids, for example halides, especially hydrochlorides, lactates, sulfates, citrates, tartrates, acetates, phosphates, methylsulfonates, p-toluenesulfonates.

The compounds I are substituted acylguanidines.

The prominent representative of the acylguanidines is the pyrazine derivative amiloride which is used in therapy as potassium-sparing diuretic. Numerous other compounds of the amiloride type are described in the literature, such as, for example, dimethylamiloride or ethylisopropyl amiloride.

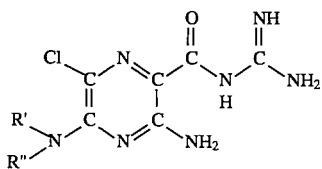

Amiloride: R', R"=H

Dimethylamiloride: R', R"=CH₃

Ethylisopropylamiloride: R'=C₂H₅, R"=CH(CH₃)₂

Furthermore, investigations indicating that amiloride has antiarrhythmic properties have been reported (Circulation 79, 1257–63 (1989)). However, wide use as antiarrhythmic agent is prevented by the fact that this effect is only weak and is accompanied by a blood pressure-lowering and saluretic effect, and these side effects are unwanted in the treatment of cardiac rhythm disturbances.

Indications of antiarrhythmic properties of amiloride have also been obtained in experiments on isolated animal hearts (Eur. Heart J. 9 (suppl.1): 167 (1988) (book of abstracts)). Thus, for example, it has been found in rat hearts that it was possible completely to suppress artificially induced ventricular fibrillation by amiloride. Even more potent than amiloride in this model was the abovementioned amiloride derivative ethylisopropylamiloride.

U.S. Pat. No. 5,091,394 (HOE 89/F 288) and European Published Application 0,556,674 (HOE 92/F 034) describe benzoylguanidines. U.S. Pat. No. 3,780,027 claims acylguanidines derived from commercially available loop diuretics such as bumetanide. Correspondingly, a potent salidiuretic activity is reported for these compounds.

It was therefore surprising that the compounds according to the invention have no unwanted and disadvantageous salidiuretic but very good antiarrhythmic properties, particularly in situations, as they occur, for example, as manifestations of oxygen deficiency. As a consequence of their pharmacological properties, the compounds are outstandingly suitable as antiarrhythmic pharmaceuticals with cardioprotective component for infarct prophylaxis and infarct treatment, and for the treatment of angina pectoris, in which case they also preventively inhibit or greatly reduce the pathophysiological processes in the development of ischemia-induced damage, especially in the induction of ischemia-induced cardiac arrhythmias. Because of their protective effects in pathological hypoxic and ischemic situations, the compounds of the formula I according to the invention can, as a consequence of inhibition of the cellular Na⁺/H⁺ exchange mechanism, be used as pharmaceuticals for the treatment of all acute or chronic ischemia-induced damage or disorders induced primarily or secondarily thereby. This relates to their use as pharmaceuticals for surgical interventions, for example in organ transplants, in which case the compounds can be used both to protect the organs in the donor before and during removal, to protect removed organs, for example on treatment with or storage thereof in physiological bath fluids, as well as on transfer into the recipient organism. The compounds are likewise valuable pharmaceuticals with a protective action when performing angioplastic surgical interventions, for example on the heart as well as on peripheral vessels. In accordance with their protective action on ischemia-induced damage, the compounds are also suitable as pharmaceuticals for the treatment of ischemias of the nervous system, especially of the CNS, and they are suitable, for example, for the treatment of stroke or of cerebral edema. In addition, the compounds of the formula I according to the invention are likewise suitable for treating types of shock, such as, for example, allergic, cardiogenic, hypovolemic and bacterial shock.

Furthermore, the compounds of the formula I according to the invention are distinguished by a potent inhibiting effect on proliferation of cells, for example fibroblast cell proliferation and proliferation of smooth vascular muscle cells. For this reason, the compounds of the formula I are suitable as valuable therapeutic agents for diseases in which cell proliferation is a primary or secondary cause, and can therefore be used as antiatherosclerotics, agents to prevent late complications of diabetes, cancers, fibrotic disorders such as pulmonary fibrosis, hepatic fibrosis or renal fibrosis, organ hypertrophies and hyperplasias, especially for prostate hyperplasia and prostate hypertrophy.

The compounds according to the invention are valuable inhibitors of the cellular sodium/proton antiporter (Na⁺/H⁺ exchanger), which is elevated in many disorders (essential hypertension, atherosclerosis, diabetes, etc.) even in cells which are easily amenable to measurements, such as, for example, in erythrocytes, platelets or leukocytes. The compounds according to the invention are therefore suitable as excellent and simple scientific tools, for example in their use as diagnostic agents for determining and differentiating different types of hypertension, but also of atherosclerosis, of diabetes, proliferative disorders, etc. Furthermore, the compounds of the formula I are suitable for preventive therapy to prevent the genesis of high blood pressure, for example essential hypertension.

Pharmaceuticals which contain a compound I can moreover be administered orally, parenterally, intravenously, rectally or by inhalation, with the preferred administration depending on the particular manifestation of the disease. The compounds I can moreover be used alone or together with pharmaceutical ancillary substances, both in veterinary and in human medicine.

The particular ancillary substances suitable for the required pharmaceutical formulation are familiar to the skilled person on the basis of his expert knowledge. Besides solvents, gel formers, suppository bases, tablet ancillary substances and other active substance vehicles, it is possible to use, for example, antioxidants, dispersants, emulsifiers, antifoam agents, masking flavors, preservatives, solubilizers or colorants.

For a form for oral use, the active compounds are mixed with the additives suitable for the purpose, such as excipients, stabilizers or inert diluents, and converted by conventional methods into suitable dosage forms such as tablets, coated tablets, hard gelatin capsules, aqueous, alcoholic or oily solutions. Examples of inert vehicles which can be used are gum arabic, magnesia, magnesium carbonate, potassium phosphate, lactose, glucose or starch, especially corn starch. Preparation can, moreover, take place either as dry or as wet granules. Examples of suitable oily vehicles or solvents are vegetable or animal oils such as sunflower oil or fish liver oil.

For subcutaneous or intravenous administration, the active compounds are converted, if required with the substances customary for this purpose, such as solubilizers, emulsifiers or other ancillary substances, into a solution, suspension or emulsion. Examples of suitable solvents are: water, physiological saline-solution or alcohols, for example ethanol, propanol, glycerol, as well as sugar solutions such as glucose or mannitol solutions, or else a mixture of the various solvents mentioned.

Examples of suitable pharmaceutical formulations for administration in the form of aerosols or sprays are solutions, suspensions or emulsions of the active substance of the formula I in a pharmaceutically acceptable solvent, such as, in particular, ethanol or water, or a mixture of such solvents.

The formulation can, if required, also contain other pharmaceutical ancillary substances such as surfactants, emulsifiers and stabilizers, as well as a propellant gas. A preparation of this type normally contains the active substance in a concentration of about 0.1 to 10, in particular about 0.3 to 3,% by weight.

The dosage of the active substance of the formula I to be administered and the frequency of administration depend on the potency and duration of action of the compounds used additionally on the nature and severity of the disease to be treated, and on the sex, age, weight and individual response of the mammal to be treated. On average, the daily dose of a compound of the formula I for a patient weighing about 75 kg is at least 0.001 mg/kg, preferably 0.01 mg/kg, up to a maximum of 10 mg/kg, preferably 1 mg/kg, of bodyweight. For acute episodes of the disease, for example immediately after suffering a myocardial infarct, higher and, in particular, more frequent dosages may also be necessary, for example up to 4 single doses per day. Up to 200 mg per day may be necessary, especially on i.v. use, for example for an infarct patient in intensive care.

| List of abbreviations: | |
| --- | --- |
| MeOH | Methanol |
| DMF | N,N-Dimethylformamide |
| RT | Room temperature |
| EA | Ethyl acetate (EtOAc) |
| m.p. | Melting point |
| THF | Tetrahydrofuran |
| eq. | Equivalent |

Experimental part

General method for preparing aroylguanidines (I) Variant A: from carboxylic acids (II, L=OH)

1.0 eq. of the carboxylic acid derivative of the formula II is dissolved or suspended in anhydrous THF (5 ml/mmol), and then 1.1 eq. of carbonyldiimidazole are added. After stirring at RT for 2 hours, 5.0 eq. of guanidine are introduced into the reaction solution. After stirring overnight, the THF is removed by distillation under reduced pressure (Rotavapor), water is added, the pH is adjusted to 6 to 7 with 2N HCl, and the corresponding acylguanidine (formula I) is filtered off. The acylguanidines obtained in this way can be converted by treatment with aqueous, methanolic or ethereal hydrochloric acid or other pharmacologically suitable acids into the corresponding salts.

General method for the preparation of aroylguanidines (I) Variant B: from alkyl carboxylates (II, L=O-alkyl)

1.0 eq. of the alkyl carboxylate of the formula II and 5.0 eq. of guanidine (free base) are dissolved in isopropanol or suspended in THF and heated to reflux until conversion is complete (thin-layer check) (typical reaction time 2 to 5 h). The solvent is removed by distillation under reduced pressure (Rotavapor), the residue is taken up in EA, and the solution is washed 3× with NaHCO$_3$ solution. It is dried over Na$_2$SO$_4$, and the solvent is removed by distillation in vacuo, and chromatography is carried out on silica gel with a suitable mobile phase, for example EA/MeOH 5:1. (For salt formation, see variant A)

EXAMPLE 1

1,1-Dioxo-3-phenyl-2H-1,2-benzothiazine-7-carbonyl guanidine hydrochloride

Colorless crystals, m.p. 271°–73° C.

Synthetic route a) 4-Bromo-3-chlorosulfonylbenzoic acid from 4-bromobenzoic acid by heating at 120° C. in pure chlorosulfonic acid for 9 h. Pouring onto ice yields colorless crystals, m.p. 185°–190° C.

b) 4-Bromo-3-sulfamoylbenzoic acid from a) by aminolysis in liquid ammonia at –40° C. and subsequent warming to RT. Aqueous workup gives colorless crystals, m.p. >250° C.

c) Methyl 4-bromo-3-sulfamoylbenzoate from b) by esterification in methanol in the presence of acetyl chloride, colorless crystals, m.p. 151° C.

d) Methyl 4-phenylalkynyl-3-sulfamoylbenzoate from c) by Stephans-Castro coupling with 2.5 equivalents of phenylacetylene, stirring at RT for 24 h in the presence of catal. (5 mol %) bis(triphenylphosphine)palladium(II) chloride, 15 mol % copper(I) iodide and 3 equivalents of n-butylamine, workup with aqueous ammonium chloride, extraction with ethyl acetate and subsequent column chromatography on silica gel with ethyl acetate/n-heptane, colorless crystals, m.p. 142° C.

e) Methyl 1,1-dioxo-3-phenyl-2H-1,2-benzothiazine-7-carboxylate from d) by Hg(OAc)$_2$-promoted cyclization in glacial acetic acid in the presence of conc. sulfuric acid at room temperature for 3 hours. Filtration with suction and trituration in ether yields colorless crystals, m.p. 240° C.

f) 1,1-Dioxo-3-phenyl1-2H-1,2-benzothiazine- 7-carbonylguanidine hydrochloride from e) by general method B

EXAMPLE 2

3-cyclohexyl-1,1-dioxo-2H-1,2-benzothiazine-7-carbonylguanidine hydrochloride

Colorless crystals, m.p. 265°–67° C.
Synthetic route a) Methyl 4-cyclohexylalkynyl-3-sulfamoylbenzoate from 1 c) in analog to process 1 d) by using cyclohexylacetylene, colorless crystals, m.p. 115°–18° C.

b) Methyl 3-cyclohexyl-1,1-dioxo-2H-1,2-benzothiazine-7-carboxylate from a) in analogy to process 1 d), colorless crystals, m.p. 170°–72° C.

c) 3-cyclohexyl-1,1-dioxo-2H-1,2-benzothiazine- 7-carbonylguanidine hydrochloride from b) by general method B

EXAMPLE 3

3-t-Butyl-1,1-dioxo-2H-1,2-benzothiazine- 7-carbonylguanidine hydrochloride

Colorless crystals, m.p. 265° C.
Synthetic route a) Methyl 4-t-butylalkynyl-3-sulfamoylbenzoate from 1 c) in analogy to process 1 d) but using t-butylacetylene, colorless crystals, m.p. 161°–63° C.

b) Methyl 3-t-butyl-1,1-dioxo-2H-1,2-benzothiazine-7-carboxylate from a) in analogy to process 1 e) colorless crystals, m.p. 132° C.

c) 3-t-Butyl-1,1-dioxo-2H-1,2-benzothiazine-7-carbonylguanidine hydrochloride from b) by general method B

EXAMPLE 4

1,1-Dioxo-2-methyl-3-phenyl-2H-1,2-benzothiazine-7-carbonylguanidine hydrochloride Colorless crystals, m.p. 243°–45° C.
Synthetic route a) Methyl 4-bromo-3-(N-methylsulfamoyl)benzoate from methyl 4-bromo-3-chlorosulfonylbenzoate in analogy to process 1 b) but using methylamine, colorless crystals, m.p. 167°–69° C.

b) Methyl 4-(Phenylethynyl)-3-(N-methylsulfamoyl)benzoate from a) in analogy to process 1 d), colorless crystals, m.p. 165°–67° C.

c) Methyl 1,1-dioxo-2-methyl-3-phenyl-2H-1,2-benzothiazine- 7-carboxylate from a) in analogy to process 1 e), colorless crystals, m.p. 145°–47° C.

d) 1,1-Dioxo-2-methyl-3-phenyl-2H-1,2-benzothiazine-7-carbonylguanidine hydrochloride from c) by general method B

EXAMPLE 5

2-Methyl-3-phenyl-1-oxo-1,2-dihydroisoquinoline- 7-carbonylguanidine hydrochloride Colorless crystals, m.p. 248°–50° C.
Synthetic route a) 4-Bromoisophthalic acid bismethylamide from 4-bromoisophthaloyl chloride in analogy to process 1 b) but using methylamine, colorless crystals, m.p. 185°–89° C.

b) 4-(Phenylethynyl)isophthalic acid bismethylamide from a) in analogy to process 1 d), colorless crystals, m.p. 156°–59° C.

c) 2-Methyl-3-phenyl-1-oxo-1,2-dihydroisoquinoline-7-carbonylmethylamine and 3-phenyl-1-oxo-1,2-dihydroiso-quinoline-7-carbonylmethylamine from b) in analogy to process 1 e), colorless crystals, m.p. 216°–19° C.

d) 2-Methyl-3-phenyl-1-1-oxo-1,2-dihydroisoquinoline-7-carboxylic acid from 2-methyl-3-phenyl-1-1-oxo-1,2-dihydroisoquinoline- 7-carbonylmethylamine with 2N KOH (aqueous) in methanol at 60° C. for 5 h, colorless crystals, m.p. 229°–31° C.

e) 2-Methyl-3-phenyl-1-oxo-1,2-dihydroisoquinoline-7-carbonylguanidine hydrochloride from d) by general method A

EXAMPLE 6

3-Phenyl-1-oxo-1,2-dihydroisoquinoline-7-carbonylguanidine hydrochloride, colorless crystals, m.p. 260°–62° C.
Synthetic route a) 3-Phenyl-1-oxo-1,2-dihydroisoquinoline-7-carboxylic acid from 3-phenyl-1-oxo-1,2-dihydroisoquinoline-7-carbonyl-methylamine (5c) in analogy to process 5d), colorless crystals, m.p. 227°–30° C.

b) 3-Phenyl-1-oxo-1,2-dihydroisoquinoline-7-carbonylguanidine hydrochloride from a) by general method A Pharmacological data Inhibition of the $Na^+/H^+$ exchanger of rabbit erythrocytes White New Zealand rabbits (Ivanovas) received a standard diet containing 2% cholesterol for six weeks in order to activate $Na^+/H^+$ exchange and thus to be able to determine the $Na^+$ influx into the erthrocytes via $Na^+/H^+$ exchange by flame photometry. The blood was taken from the ear arteries and anticoagulated by 25 IU of potassium heparin. A portion of each sample was used for duplicate determination of the hematocrit by centrifugation. Aliquots each of 100µl were used to measure the initial $Na^+$ content of the erythrocytes.

In order to determine the amiloride-sensitive sodium influx, 100µl of each blood sample were incubated in each case in 5 ml of a hyperosmolar salt/sucrose medium (mmol/1: 140 NaCl, 3 KCl, 150 sucrose, 0.1 ouabain, 20 tris(hydroxymethyl)aminomethane) at pH 7.4 and 37° C. The erythrocytes were then washed three times with ice-cold $MgCl_2$/ouabain solution (mmol/1: 112 $MgCl_2$, 0.1 ouabain) and hemolyzed in 2.0 ml of distilled water. The intracellular sodium content was determined by flame photometry.

The net $Na^+$ influx was calculated from the difference between initial sodium levels and the sodium content of the erthrocytes after incubation. The sodium influx which could be inhibited by amiloride emerged from the difference in the sodium content of the erythrocytes after incubation with and without amiloride $3\times10^{-4}$ mol/1. The procedure with the compounds according to the invention was the same.

Results

Inhibition of the $Na^+/H^+$ exchanger:
Example 1: $IC_{32}=0.9\times10^{-6}$ mol/l
Example 2: $IC_{32}=0.5\times10^{-6}$ mol/l

I claim:
1. An acylguanidine of the formula I

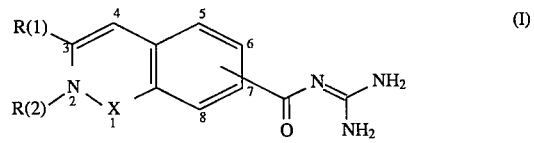

in which:

X is carbonyl, sulfonyl,

R(1) is H, $(C_1-C_8)$-alkyl, unsubstituted or substituted by hydroxyl, $(C_3-C_8)$-cycloalkyl, phenyl, which is unsubstituted or substituted by 1–3 substituents from the group consisting of F, Cl, $CF_3$, $CH_3$, methoxy, hydroxyl, amino, methylamino or dimethylamino, R(2) is H, $(C_1-C_4)$-alkyl, and the pharmaceutically suitable salts thereof.

2. A compound of the formula I as claimed in claim 1, in which:

X is sulfonyl,

R(1) is H, $(C_1-C_8)$-alkyl, unsubstituted or substituted by hydroxyl, $(C_3-C_8)$-cycloalkyl, phenyl, which is unsubstituted or substituted by 1–3 substituents from the group consisting of F, Cl, $CF_3$, $CH_3$, methoxy, hydroxyl, amino, methylamino, dimethylamino, R(2) is H, $(C_1-C_4)$-alkyl.

3. A compound of the formula I as claimed in claim 1, in which the carbonyl guanidide [—CO—N=C(NH$_2$)$_2$] is situated in position 7 on the particular benzene nucleus.

4. A method for the treatment of arrhythmias, which comprises administration of an effective amount of a compound I as claimed in claim 1 mixed with the conventional additives and in a suitable dosage form.

5. A pharmaceutical composition for the treatment of arrhythmias which comprises an amount of a compound of formula I as claimed in claim 1 effective for said treatment, together with a pharmaceutically acceptable carrier.

6. A method for the treatment or prophylaxis of myocardial infarct which comprises administering to a host in need of said treatment an effective amount of a compound of the formula I as claimed in claim 1.

7. A method for the treatment or prophylaxis of angina pectoris which comprises administering to a host in need of said treatment an effective amount of a compound of the formula I as claimed in claim 1.

8. A method for the treatment or prophylaxis of ischemic heart conditions which comprises administering to a host in need of said treatment an effective amount of a compound of the formula I as claimed in claim 1.

9. A method for the treatment or prophylaxis of ischemic conditions of the peripheral and central nervous systems and of stroke which comprises administering to a host in need of said treatment an effective amount of a compound of the formula I as claimed in claim 1.

10. A method for the treatment or prophylaxis of ischemic conditions of the peripheral organs and limbs which comprises administering to a host in need of said treatment an effective amount of a compound of the formula I as claimed in claim 1.

11. A method for the treatment of states of shock which comprises administering to a host in need of said treatment an effective amount of a compound of the formula I as claimed in claim 1.

12. A method for protective treatment in surgical operations and organ transplantations which comprises administering to a host in need of said treatment an effective amount of a compound of the formula I as claimed in claim 1.

13. A method for the preservation and storage of transplants for surgical procedures which comprises treating said transplants with an effective amount of a compound of the formula I as claimed in claim 1.

14. A method for the treatment of diseases in which cell proliferation is a primary or secondary cause which comprises administering to a host in need of said treatment an effective amount of a compound of the formula I as claimed in claim 1.

15. A method as claimed in claim 29, wherein the disease is atherosclerosis, a fibrotic disorder or prostate hyperplasia.

16. A method as claimed in claim 31, wherein the fibrotic disorder is pulmonary fibrosis, fibrosis of the liver or fibrosis of the kidneys.

17. A diagnostic agent for the inhibition of the Na+/H+ exchanger and the diagnosis of hypertension and proliferative disorders which comprises a compound of the formula I as claimed in claim 1.

18. A pharmaceutical composition for the treatment of myocardial infarct, angina pectoris, ischemic conditions of the heart, of the peripheral and central nervous systems, of the peripheral organs and limbs, of stroke and of states of shock which comprises an effective amount for said treatment of a compound of formula I as claimed in claim 1 together with a pharmaceutically acceptable carrier.

* * * * *